United States Patent [19]

Shimizu

[11] 3,956,503

[45] May 11, 1976

[54] COMPOSITION FOR THE TREATMENT AND THE PREVENTION OF HELIENCEPHALITIS, THERMOPLEGIA AND OTHER DISORDERS IN DOMESTIC ANIMALS AND POULTRY

[75] Inventor: Eiichi Shimizu, Irima, Japan

[73] Assignee: Daiichi Seiyaku Co., Ltd., Tokyo, Japan

[22] Filed: Oct. 11, 1973

[21] Appl. No.: 405,494

[30] Foreign Application Priority Data

Oct. 12, 1972   Japan.............................. 47-102246

[52] U.S. Cl............................... 424/305; 424/309; 424/315; 424/319
[51] Int. Cl.².................................. A61L 31/215
[58] Field of Search ............ 424/310, 311, 305, 319

[56] References Cited
OTHER PUBLICATIONS

Gofman – Chem. Abst., Vol. 69 (1968) p. 9601d.
Halina – Chem. Abst., Vol. 74 (1971) p. 139,303x.
Chem. Abst., Seventh Collective Index, Vol. 56–65 (1962–1966) pp. 10,959s & 10,960s.
Bertelli et al., Chem. Abstracts, Vol. 66 (1967), p. 1297v.
Shigemi, Chem. Abstracts, Vol. 72 (1970), p. 53688y.
Wilde et al., Chem. Abstracts, Vol. 76 (1972), p. 94,779e.

*Primary Examiner*—V. D. Turner
*Attorney, Agent, or Firm*—Oblon, Fisher, Spivak, McClelland & Maier

[57] ABSTRACT

Heliencephalitis, thermoplegia and disorders resulting from fighting among animals and poultry are effectively treated and prevented by the administration of at least one compound selected from the group consisting of trans-4-aminomethylcyclohexanecarboxylic acid, 4-aminomethylbenzoic acid, $\epsilon$-aminocaproic acid and the lower alkyl esters, aryl esters and the pharmaceutically acceptable inorganic and organic salts thereof.

4 Claims, No Drawings

COMPOSITION FOR THE TREATMENT AND THE PREVENTION OF HELIENCEPHALITIS, THERMOPLEGIA AND OTHER DISORDERS IN DOMESTIC ANIMALS AND POULTRY

BACKGROUND OF THE INVENTION

1. Field of the Invention:

The present invention relates to a composition which is useful in the treatment or prevention of heliencephalitis and thermoplegia in animals and poultry and other disorders caused by fighting among domestic animals and poultry. More particularly, the present invention relates to therapeutic compositions which contain at least one active ingredient selected from the group consisting of trans-4-aminomethylcyclohexanecarboxylic acid, 4-aminomethylbenzoic acid, ε-aminocaproic acid, and the alkyl esters, aryl esters or pharmaceutically acceptable salt thereof in combination with a pharmaceutical carrier.

2. Description of the Prior Art:

In recent years, stock breeding has been practiced on an increasingly larger scale, which has resulted in the intensive breeding of a large number of domestic animals and poultry. Because of the crowded conditions, fighting among the animals or birds occurs more frequently, and the temperatures within the breeding houses increase. These factors often results in heliencephalitis or thermoplegia of domestic animals and poultry. Alternatively, the animals or birds may become feeble or die as a result of injuries suffered from the increased amount of fighting which occurs. The same tendency is observed during transportation of domestic animals and poultry over long distances, because of poor ventilation during transportation, serious fatigue or fighting of the animals or birds during transit. These problems are accentuated during the summertime which results in substantial economic losses.

The cause of the heliencephalitis, thermoplegia and disorders as the result of fighting among domestic animals and poultry is believed attributable to the attack of microorganisms on the cerebral cortex, the pons Varolii, and the medulla oblongata of the animals and poultry. When domestic animals or poultry suffer from these diseases, their body temperatures increase to more than 40°C, and they develop enervation, fatigue, dizziness, and dyscinesia as premonitory symptoms. Subsequently, various cerebral problems such as anxiety, perspiration, excitation, delirium, and convulsion (tonochlonic) occur. At the same time, palpitation occurs, the pulse rate becomes weaker and more rapid, and breathing becomes labored and shorter. When these cerebral troubles fully develop, the body temperature gradually decreases.

Heliencephalitis, thermoplegioa and disorders resulting from the fighting of domestic animals and poultry are especially observed more frequently among those animals or birds which are fat or feeble. The progress of the disease is acute, and those infected collapse within less than about 20 minutes. The infected animals or birds which have collapsed remain in this state for a couple of days. Gradually, the animals or birds become feeble, and finally reach the state of delelectasis.

Heretofore, these diseases have been treated by the internal administration or the subcutaneous injection of camphor, caffeine, alcohol or ether as cardiovascular agents. However, when serious cases are treated with these agents, recovery is poor. Thus, no fully effective method of treatment has been developed for these diseases.

A need, therefore, continues to exist for an effective method for treating heliencephalitis, thermoplegia and other disorders which result from fighting in animals and poultry.

SUMMARY OF THE INVENTION

Accordingly, one object of the present invention is to provide a medicinal agent which can be effectively used for the treatment and prevention of heliencephalitis, thermoplegioa and disorders resulting from combat among domestic animals and poultry.

Briefly, this object and other objects of the invention as hereinafter will become more readily apparent can be attained by the administration of at least one of the active compounds selected from the group consisting of trans-4-aminomethylcyclohexanecarboxylic acid, 4-aminomethylbenzoic acid, and ε-aminocaproic acid and the lower alkyl esters, aryl esters or pharmaceutically active salts thereof.

DETAILED DESCRIPTION OF THE PREFERRED EMBODIMENTS

The fact that trans-4-aminomethylcyclohexanecarboxylic acid, 4-aminomethylbenzoic acid and ε-aminocaproic acid and the lower alkyl esters, aryl esters and salts thereof are effective in the treatment and the prevention of heliencephalitis, thermoplegia and disorders resulting from fighting among animals and birds is surprising since it has been believed that these compounds have not been effective for the treatment of nervous disorders. Although they are known as excellent antiplasmin drugs in the realm of human medicine, heretofore they have only been useful for the treatment of sores in domestic animals. It was a surprise, therefore, when these compounds were found to be useful for the treatment and prevention of heliencephalitis, thermoplegia and disorders resulting from fighting among animals and poultry. Consequently, the medicinal properties of these compounds offer a significant advantage for the stock breeding industry.

The compounds of this invention do not exhibit undesirable side-effects and they can be administered intravenously by injection or orally, or the compounds can be admixed with animal feeds. The drugs are effective almost immediately when administered and no resistance to the medicine is observed. Furthermore, the drugs are very effective in the treatment of the diseases even at such surprisingly small dosages as 1 to 100 mg/Kg/day, preferably 2 to 10 mg/Kg/day, as compared with known agents. For example, when swine are treated, 25 mg/Kg/day is an effective dose rate.

The compounds of this invention can be used as the acids, as the lower alkyl esters containing 1 to 8 carbon atoms or as aryl esters such as the phenyl, benzyl, p-methylphenyl and p-methylbenzyl esters, or as a pharmaceutically acceptable inorganic salt such as the sodium, potassium, or calcium salt or a pharmaceutically acceptable organic salt. Although the compounds of the present invention have been found to be useful in the treatment of heliencephalitis, thermoplegia and disorders resulting from fighting, they are also effective in preventing the diseases.

Having generally described this invention, a further understanding can be obtained by reference to certain specific examples which are provided herein for purposes of illustration only and are not intended to be limiting unless otherwise specified.

EXAMPLE

Five percent aqueous solutions of trans-4-aminomethylcyclohexanecarboxylic acid, 4-aminomethylbenzoic acid, and ε-aminocaproic acid were administered at dosage levels of 5 mg/10 Kg of body weight twice a day to swine suffering from heliencephalitis, thermoplegia, and disorders resulting from fighting in breeding farms throughout Irima City, Saitama Prefecture, Japan. The rate of cure was observed the very next day, and the results are shown in the following tables. As is clear from the data, excellent cure rates were achieved. Even those swine suffering from diplegia rapidly recovered from the disease.

TABLE I

The administration of trans-4-aminomethylcyclohexanecarboxylic acid

Heliencephalitis and thermoplegia

| | Kind of Swine | Body weight (Kg) | Amount of drug injected (ml/10Kg) | Number tested | Number cured | Rate of cure (%) | |
|---|---|---|---|---|---|---|---|
| Treated group | Y.L | 20–30 | 5 | 49 | 49 | 100 | |
| | B | 20–30 | 5 | 30 | 29 | 96.6 | 98.7 |
| | Y.B | 20–30 | 5 | 73 | 72 | 98.6 | |
| Non-treated group | Y.L | 20–30 | — | 21 | 7 | 33.3 | |

Fighting Disorder

| | Kind of Swine | Body weight (Kg) | Amount of drug injected (ml/10Kg) | Number tested | Number cured | Rate of cure (%) | |
|---|---|---|---|---|---|---|---|
| Treated group | Y.L | 40–70 | 5 | 16 | 16 | 100 | |
| | B | 40–70 | 5 | 12 | 12 | 100 | 100 |
| | Y.B | 40–70 | 5 | 3 | 3 | 100 | |
| Non-treated group | Y.L | 40–70 | — | 18 | 3 | 16.6 | |

TABLE II

The administration of 4-aminomethylbenzoic acid

Heliencephalitis and thermoplegia

| | Kind of Swine | Body weight (Kg) | 4-aminomethylbenzoic acid (ml/10Kg) | Number tested | Number cured | Rate of cure (%) | |
|---|---|---|---|---|---|---|---|
| Treated group | Y.L | 20–30 | 5 | 38 | 37 | 97.4 | |
| | B | 20–30 | 5 | 28 | 28 | 100 | 97.5 |
| | Y.B. | 20–30 | 5 | 40 | 38 | 95.0 | |
| Non-treated group | Y.L | 20–30 | — | 12 | 3 | 25 | |

Fighting Disorders

| | Kind of Swine | Body weight (Kg) | 4-aminomethylbenzoic acid (ml/10Kg) | Number tested | Number cured | Rate of cure (%) | |
|---|---|---|---|---|---|---|---|
| Treated group | Y.L | 20–30 | 5 | 13 | 13 | 100 | |
| | B | 20–30 | 5 | 10 | 10 | 100 | 100 |
| | Y.B. | 20–30 | 5 | 12 | 12 | 100 | |
| Non-treated group | Y.L | 20–30 | — | 15 | 2 | 13.3 | |

TABLE III

The administration of ε-aminocaproic acid

Heliencephalitis and thermoplegia

| | Kind of Swine | Body weight (Kg) | ε-aminocaproic acid (ml/10Kg) | Number tested | Number cured | Rate of cure (%) | |
|---|---|---|---|---|---|---|---|
| Treated group | Y.L | 20–30 | 5 | 40 | 40 | 100 | |
| | B | 20–30 | 5 | 30 | 30 | 100 | 97.7 |
| | Y.B | 20–30 | 5 | 29 | 27 | 93.1 | |
| Non-treated group | Y.L | 20–30 | — | 14 | 2 | 14.3 | |

TABLE III-continued

The administration of ε-aminocaproic acid

| | Kind of Swine | Body weight (Kg) | Heliencephalitis and thermoplegia | | | |
| --- | --- | --- | --- | --- | --- | --- |
| | | | ε-amino-caproic acid (ml/10Kg) | Number tested | Number cured | Rate of cure (%) |

| | Kind of Swine | Body weight (Kg) | Fighting Disorders | | | |
| --- | --- | --- | --- | --- | --- | --- |
| | | | ε-amino-caproic acid (ml/10Kg) | Number tested | Number cured | Rate of cure (%) |
| Treated group | Y.L | 20–30 | 5 | 17 | 17 | 100 ⎫ |
| | B | 20–30 | 5 | 18 | 18 | 100 ⎬ 100 |
| | Y.B | 20–30 | 5 | 19 | 19 | 100 ⎭ |
| Non-treated group | Y.L | 20–30 | — | 11 | 2 | 18.2 |

The kinds of swine treated were as follows:
Y.L: Yorkshire x Landrace
B: Berkshire
Y.B: Yorkshire x Berkshire

Having now fully described this invention, it will be apparent to one of ordinary skill in the art that many changes and modifications can be made thereto without departing from the spirit or scope of the invention as set forth herein.

What is claimed as new and intended to be covered by Letters Patent is:

1. A method for the treatment of heliencephalitis, thermoplegia, and increased body temperature arising from the fighting of domestic animals, which comprises:
   administering trans-4-aminomethylcyclohexanecarboxylic acid, a lower alkyl ester, an aryl ester or a pharmaceutically acceptable inorganic or organic salt thereof to said animals in an amount ranging from 1 to 100 mg/kg/day.

2. The method of claim 1 wherein the domestic animals are poultry.

3. A method for the treatment of heliencephalitis, thermoplegia and increased body temperature arising from the fighting of domestic animals, which comprises:
   administering 4-aminomethylbenzoic acid, a lower alkyl ester, an aryl ester or a pharmaceutically acceptable inorganic or organic salt thereof to said animals in an amount ranging from 1 to 100 mg/kg/day.

4. The method of claim 3 wherein domestic animals are poultry.

* * * * *